United States Patent [19]

Betush

[11] 4,372,307

[45] Feb. 8, 1983

[54] PINCH VALVE SYRINGE

[75] Inventor: Frank A. Betush, Carson, Calif.

[73] Assignee: Progressive Machine Products, Inc., Carson, Calif.

[21] Appl. No.: 280,307

[22] Filed: Jul. 6, 1981

[51] Int. Cl.³ .............................................. A61M 3/00
[52] U.S. Cl. .................................... 128/224; 128/274; 251/7
[58] Field of Search ....................... 128/224, 274, 231; 251/7, 9, 10; 222/529, 527, 526

[56] References Cited

U.S. PATENT DOCUMENTS

| 541,865 | 7/1895 | Lundholm | 251/10 |
| 3,913,882 | 10/1975 | Moulet | 251/9 |
| 3,970,225 | 7/1976 | Jeal et al. | 251/9 X |
| 4,097,020 | 6/1978 | Sussman | 251/10 |
| 4,149,315 | 4/1979 | Page, Jr. et al. | 128/224 X |
| 4,245,812 | 1/1981 | Burger | 251/10 |

Primary Examiner—John D. Yasko
Attorney, Agent, or Firm—Keith D. Beecher

[57] ABSTRACT

A syringe is provided which is particularly useful in dental work, but which has general utility. The syringe includes pinch valves, and it is constructed to be simple and inexpensive, requiring a minimum of components, and yet to be highly reliable. The syringe is capable of emitting, for example, a stream of air and water, or other fluids or particulate matter, each of which is independently controlled, and neither of which has any tendency to be emitted when only the other is required.

4 Claims, 5 Drawing Figures

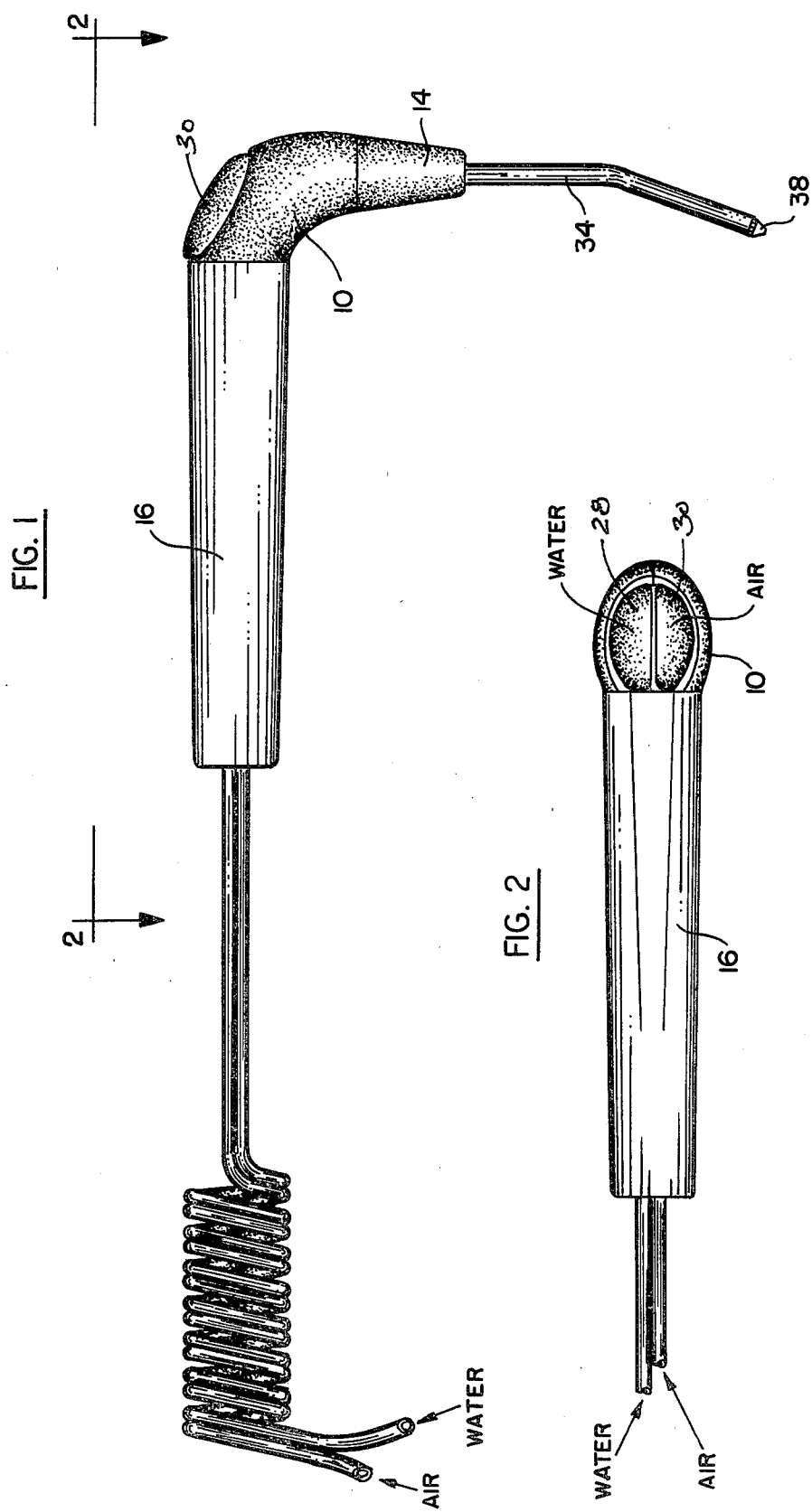

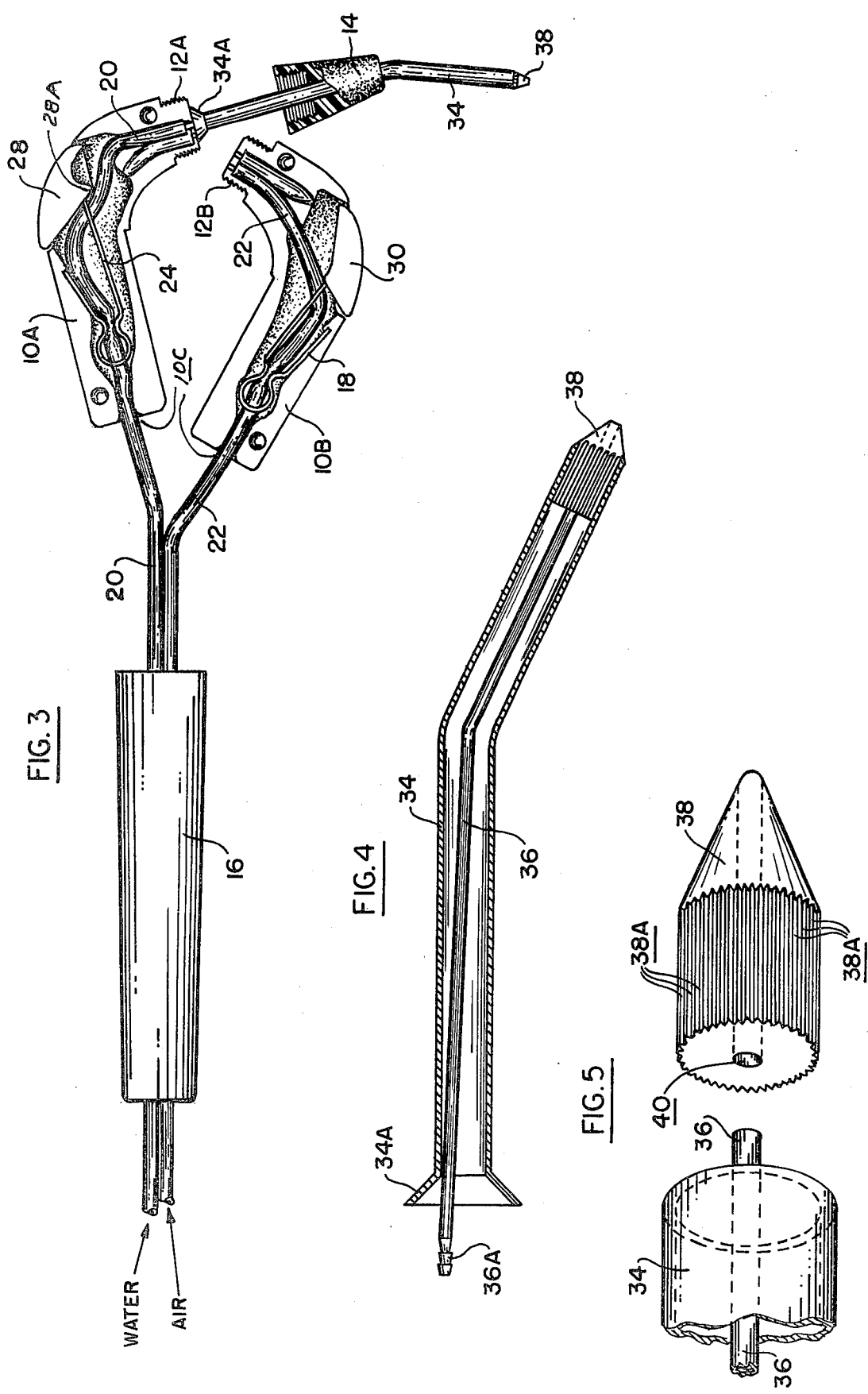

PINCH VALVE SYRINGE

BACKGROUND OF THE INVENTION

The syringe of the invention is generally similar to the syringe described in U.S. Pat. No. 4,108,178 which issued Aug. 22, 1978 in the name of the present inventor and which is assigned to the present assignee.

As described in the patent, the usual syringes available prior to the subject matter of the patent include pushbutton valves to control the flow of streams of compressed air and water to a nozzle which is mounted on one end of the instrument, the valves being sealed by O-rings. Apart from being complex and expensive, the prior art syringes have a tendency to stick due to debris in the controlled fluids. The syringe described in the patent uses pinch valves, and it is rugged in its construction, simple in its operation, inexpensive and uncomplicated, and it has no tendency to stick, even when subjected to rough usage. Additionally, the tubes may periodically be shifted to new pinch points to prolong tube life.

As mentioned above, the syringe of the present invention, like the syringe disclosed in the patent, is a pinch valve type of syringe, and it exhibits all the advantages of the syringe disclosed in the patent. In addition, the syringe of the present invention is simpler in its construction than the syringe disclosed in the patent, and is sturdier and more reliable. Moreover, the syringe of the invention incorporates certain features which are not found in the syringe of the patent, and which will be described in the following specification.

The syringe of the present invention, as mentioned above, may be used to control a wide variety of liquids, gases, and particulate matter, and it has a wide range of utility apart from dental work, for variably and proportionately metering and dispensing a multiplicity of different liquids.

BRIEF DESCRIPTION OF THE DRAWINGS

FIG. 1 is a side view of a syringe constructed in accordance with the invention;

FIG. 2 is a top plan view of the syringe of FIG. 1, taken along the line 2—2 of FIG. 1;

FIG. 3 is a further view of the syringe, with the handle withdrawn, and with the body portion open to reveal the internal operating components;

FIG. 4 is a sectional view of a nozzle which is mounted on the end of the syringe remote from the handle; and FIG. 5 is a detached perspective view of a tip element which is used in the nozzle of FIG. 4 to permit, for example, water and air to be emitted independently through the tip of the syringe, or by depressing both buttons, proportionally metering and dispensing a variable mixture or mist of both fluids.

DETAILED DESCRIPTION OF THE ILLUSTRATED EMBODIMENT

The syringe shown in the drawing includes a molded sterilizable plastic body 10 shown in FIGS. 1 and 2, and which is made up of two sections 10A and 10B, as shown in FIG. 3. The two sections 10A and 10B have threads 12A and 12B at their ends, and a nut 14 is threaded onto the threads to hold the body sections 10A and 10B together.

The syringe also includes an open-ended tubular handle 16 which may be composed, for example, of stainless steel. The handle 16 slips over the other end of the body 10, to assist the nut 14 to hold the body sections 10A, 10B together.

A pair of springs 24 and 18 are mounted in the respective body sections 10A and 10B, and these springs are bent back on each other, as shown. A pair of tubes 20 and 22 extend through respective channels 10C in the respective body sections 10A and 10B, and through the springs 24 and 18. The channels grip the tubes and act as a strain relief against abrasive pulling of the tubes. The springs are configured so that normally they pinch the tubes 20 and 22. A button 28 is molded to the end of spring 24, and a button 30 is molded to the end of spring 18. When button 28 is depressed, the spring 24 releases tube 20, and the fluid, such as water, for example, is free to flow through the tube. When the button 30 is depressed, the spring 18 releases the tube 22, and a fluid, such as air is free to flow through the latter tube. A fine, variable flow control is possible proportionate to the amount the buttons are depressed.

A nozzle 34 is slidable in nut 14, and it has a flared end 34A which holds the nozzle within the nut when the nut is screwed onto the threads 12A and 12B. The nozzle may be rotated through 360° with respect to the nut 14. The nozzle 34 includes an internal tube 36 which extends through the nozzle, as shown in FIG. 4, and has an end 36A which is appropriately serrated. The end 36A of the nozzle is inserted into the end of tube 20, so that the water flowing through tube 20 is caused to flow through tube 36, and out through the center of tip 38, which is mounted on the end of nozzle 34. The nozzle 34, tube 36 and tip 38 may all be composed, for example, of stainless steel.

The tip 38 has the configuration shown in FIG. 5, and includes a central hole 40 into which the end of tube 36 may be inserted. It will be appreciated that when the button 28 is depressed to release spring 16, the water flows through the tube 20, and into tube 36, and out the center of tip 38. The end of tube 20 which receives the end 36A of tube 36 has convolutions, which are received in corresponding convolutions formed in the end of body sections 10A and 10B, and which serve firmly to force the tube 20 into intimate contact with the end of 36A of tube 36 to assure that there will be no leakage of water.

The end of tube 22 is similarly supported in the end of the tubular body 10 by convolutions in the sections 10A and 10B in position such that the end of the tube 22 is held adjacent to the flared end of nozzle 34. Then, when button 30 is depressed to release the tube 22, air is blown through the nozzle 34 and through passages 38A along the periphery of tip 38, so that air is emitted around the periphery of the tip, whenever the button 30 is depressed. As the air stream tends to follow the tips 38 conical shape, it additionally entrains surrounding air into the stream, thereby enhancing the total volume of air flow directed at a target.

The syringe described above is highly reliable, in that the springs 16 and 18 pinch against themselves for a positive pinching action exerting no forces on any other components when normally pinched, and eliminating any requirement for separate bars, as are used in the prior art units. Also, for economy reasons, the buttons 28 and 30 are snapfitted directly on the ends of the springs. The entire unit may be dismantled without tools, merely by loosening the nut 14, and sliding the handle 16 back from the body 10. The springs and buttons may then be removed easily, and without tools, for repair, replacement, or for sterilization purposes. All components may be constructed of sterilizable materials as required.

A self-sealing action for the tubes 22 and 20 is provided when nut 14 is tightened, so that a highly reliable seal is obtained without any need for O-rings. Removal of nut 14 allows removal of the nozzle for cleaning and sterilization purposes.

As described, the fluids controlled by the syringe are completely separated and cannot come into contact with one another. Specifically, there is no danger of blowing water through the tip 38 when the air button 30 is operated. (A common failure in prior art items.) In the construction of the syringe, the precision molded sections 10A and 10B grip the outsides of the tubes with a series of convolutions to provide a sealed path, particularly, for the water into the inner tube 36 of nozzle 34.

A "suck back" feature is incorporated into the syringe which is similar to the feature of the control unit of U.S. Pat. No. 4,117,861 which issued Oct. 3, 1978 to the present inventor, and which is assigned to the present assignee. This suck back function in the water line prevents dripping from the tip of the syringe, and assures that when the air button 30 is operated, there will be no water in the air stream as required for drying applications.

The suck back feature is achieved by the manner in which the tube 20 is threaded through spring 24. When the button 28 is depressed it sequentially causes the forward end 28A of the button partially to deform the tube 20. Then, as the spring continues to travel it unpinches tube 20 allowing fluid to flow. When the button is released, the sequence is reversed. The first action is to squeeze the tube 20 to prevent any further water from flowing through the tube, and the further release action removes the additional squeezing effect from tube 20, causing the tube to return to normal shape and draw back on any water that may be trapped in the forward end of the tube. This function may be overridden, disarmed or varied by changing or removing the end 28A which contacts the spring and partially squeezes the tube, if the operator so desires.

It will be appreciated that while a particular embodiment of the invention has been shown and described, modifications may be made. It is intended in the claims to cover all modifications which come within the true spirit and scope of the invention.

What is claimed is:

1. A unit for controlling the flow of a fluid including: a body having first and second longitudinal sections; a first elongated resilient strip mounted in the first section of said body and bent back on itself to define a first pinch area; a first resilient tube extending through the first resilient strip and across said first pinch area to be pinched by said first resilient strip; a second elongated resilient strip mounted in the second section of said body and bent back on itself to define a second pinch area; a second resilient tube extending through the second resilient strip and across the second pinch area to be pinched by said second resilient strip; a nozzle mounted on one end of said body and including a coaxial rigid tube; with one end of said first resilient tube being fitted over one end of said rigid tube; and a nut threaded to said one end of said body in coaxial relationship with said nozzle to hold the first and second longitudinal sections together and to cause said sections to clamp and seal the first resilient tube to said one end of said rigid tube; each of said resilient strips having a free end; first and second actuating buttons respectively formed on the free ends of said resilient strips; the two sections of said body also being formed to clamp and seal the second resilient tube against the end of said nozzle when the nut is tightened, to enable the second resilient tube to emit fluid into the annular portion of said nozzle surrounding said rigid tube.

2. The unit defined in claim 1, and which includes an open-ended tubular handle fitted over the other end of the body in press fit therewith.

3. The unit defined in claim 1, in which said button formed on the free end of said first resilient strip is configured to exert a slight squeezing action on said first resilient tube at a location spaced from said first pinch area when the first resilient strip is moved to release the first resilient tube from the pinch action so as to create a suction in the first resilient tube when the resulting first resilient strip is released.

4. The unit defined in claim 1, in which said nozzle is rotatable with respect to said body.

* * * * *